(12) United States Patent
Ream

(10) Patent No.: US 8,870,568 B1
(45) Date of Patent: Oct. 28, 2014

(54) ORAL SUCTION DEVICE

(76) Inventor: Becki T. Ream, Omaha, NE (US)

(*) Notice: Subject to any disclaimer, the term of this patent is extended or adjusted under 35 U.S.C. 154(b) by 136 days.

(21) Appl. No.: 11/374,775

(22) Filed: Mar. 14, 2006

(51) Int. Cl.
*A61C 17/06* (2006.01)

(52) U.S. Cl.
USPC ................................................ 433/93

(58) Field of Classification Search
USPC .................................. 433/91, 92, 93, 96, 140
See application file for complete search history.

(56) References Cited

U.S. PATENT DOCUMENTS

| | | | | |
|---|---|---|---|---|
| 4,167,814 A | * | 9/1979 | Schubert | 433/93 |
| 4,270,531 A | * | 6/1981 | Blachly et al. | 128/207.14 |
| 4,425,911 A | * | 1/1984 | Luomanen et al. | 128/200.26 |
| 4,975,057 A | * | 12/1990 | Dyfvermark | 433/93 |
| 5,441,410 A | * | 8/1995 | Segerdal | 433/93 |
| 5,588,836 A | * | 12/1996 | Landis et al. | 433/93 |
| 5,924,866 A | * | 7/1999 | Eldreth | 433/140 |
| 6,241,521 B1 | * | 6/2001 | Garrison | 433/140 |
| 6,890,322 B2 | * | 5/2005 | Bertoch et al. | 604/174 |
| 2002/0095119 A1 | * | 7/2002 | Bertoch et al. | 604/179 |

* cited by examiner

*Primary Examiner* — Sunil K Singh
(74) *Attorney, Agent, or Firm* — Stinson Leonard Street LLP

(57) ABSTRACT

A dental device is provided with a mouth prop for selectively retaining a patient's mouth in an open position while holding the distal end of a suction tube at a desirable location within the patient's mouth for removing fluid and debris. The mouth prop may be provided with a hinge to permit the mouth prop to move between open and compressed positions. The mouth prop may be provided with bump-stops to permit movement of the hinge without crimping the suction tube. Different apertures are provided for coupling the suction tube with the mouth prop., in a variety of positions.

16 Claims, 4 Drawing Sheets

ORAL SUCTION DEVICE

BACKGROUND

Various dental procedures require polishing, drilling, grinding and other such procedures that produce residue and/or particulate. Water is used to rinse the areas of the patient's mouth and to cool areas that are being drilled or ground. As the fluid washes away the residue and particles, it typically pools within the patient's mouth. Suction tubes have long been used to remove such particulate from a patient's mouth. The common suction tube is provided with a first, distal end having a nozzle, and an opposite end that is coupled to a suction device. Oftentimes, a dental assistant or the patient must hold the suction tube in position within the patient's mouth while the dentist or hygienist perform various procedures. Other times, the water and particulate is allowed to pool within the patient's mouth for a brief period of time while work is being performed on the patient's teeth. Then the work stops, while the patient or dental hygienist positions the suction tube in the mouth to remove the fluid and particulate. This stop-and-start method of performing the dental procedures is cumbersome and time consuming. In instances where the patient or the hygienist may hold the suction tube in the mouth while work is being performed, the suction tube frequently, but unintentionally, interferes with the work being performed. Moreover, the distal end of the suction tube oftentimes comes into contact with the patient's cheek or tongue, which prevents the flow of liquid and debris into the suction tube.

Oftentimes, dental procedures can take a considerable amount of time. During the procedures the patients must keep their mouths open to enable the dentist to perform the work. This can become difficult and can tire the patient's jaw muscles rapidly, especially where the patient is elderly. Accordingly, as the procedures continue, the patient becomes more and more uncomfortable, while the patient's mouth moves closer and closer to a closed position.

Accordingly, what is needed is a new device that holds a suction tube at the optimum location within the patient's mouth, far from the area on which the dentist is working. Such a device should also serve as a mouth prop to position the patient's mouth in an open, but comfortable position, reducing strain on the patient's jaw muscles. Large and/or rigid mouth props may produce their own strain on a patient's mouth. Such mouth props can also be intimidating, as the patient feels as the mouth prop is forcing the patient's mouth into a particular position. Accordingly, a novel dental device should provide a level of deformable resiliency in order to increase patient comfort. However, such a deformable nature cannot crimp or otherwise obstruct the airway of the suction tube.

SUMMARY OF THE INVENTION

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

An oral suction device is provided for the removal of fluid and debris from a patient's mouth. The device is provided with a mouth prop that may be positioned within the individual's mouth between an upper and lower arcade of teeth on one side of the arcades (right or left) as shown in FIG. 4. The mouth prop is generally provided with a first wing member and a second wing member that are each formed to have opposite first and second end portions. The first end portions of the first and second wing members are coupled with one another so that the two wing members are disposed at an angle with respect to one another. An elongated suction tube is provided with a first end portion that is placed in communication with a source of suction. A second end portion of the tube is coupled within an aperture formed at least partially within the mouth prop.

In use, the mouth prop is positioned on one side between the patient's upper and lower arcades of teeth, with the second end portion of the tube extending from the aperture in the mouth prop to a convenient location within the patient's mouth for evacuating fluid and debris.

In one embodiment of the device, the tube is slideably positionable within the aperture to selectively locate the second end portion of the tube within the patient's mouth. The tube may also be provided to be flexible and deformable into nearly any usable shape. The aperture may be formed within the mouth prop to have a closed peripheral edge portion so that lateral movement or removal of the tube is prevented. In another embodiment, the aperture may be in communication with a sidewall of the mouth prop to permit selective insertion and removal of the tube.

In one embodiment, a hinge may be positioned closely adjacent the first end portions of the first and second wing members so that the second end portions of the first and second wing members may be selectively compressed toward one another. Bump-stops may be provided to prevent compression or kinking of the tube when the first and second wing members are compressed toward one another.

It is therefore a principal object of the present invention to provide a device for the removal of liquid and debris from a patient's mouth.

A further object of the present invention is to provide a device that simultaneously props a patient's mouth open while assisting in the removal of fluid and debris from the patient's mouth.

Still another object of the present invention is to provide a deformably resilient mouth prop that may be selectively used to hold a suction tube.

Yet another object of the present invention is to provide a hinged mouth prop for supporting a suction tube within a patient's mouth.

A further object of the present invention is to provide a hinged mouth prop having one or more bump-stops to prevent compression of a suction tube supported between the opposing wings of the mouth prop.

Still another object of the present invention is to provide a device for positioning a suction tube within a patient's mouth that does not require the patient or a dental assistant to support or position the suction tube.

Yet another object of the present invention is to provide a combination mouth prop and suction device that is relatively simple to manufacture and use.

These and other objects of the present invention will be apparent after consideration of the Detailed Description and Figures herein.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DETAILED DESCRIPTION

Embodiments are described more fully below with reference to the accompanying figures, which form a part hereof and show, by way of illustration, specific exemplary embodiments. These embodiments are disclosed in sufficient detail to enable those skilled in the art to practice the invention. However, embodiments may be implemented in many different forms and should not be construed as being limited to the embodiments set forth herein. The following detailed description is, therefore, not to be taken in a limiting sense in that the scope of the present invention is defined only by the appended claims.

Figure 4:
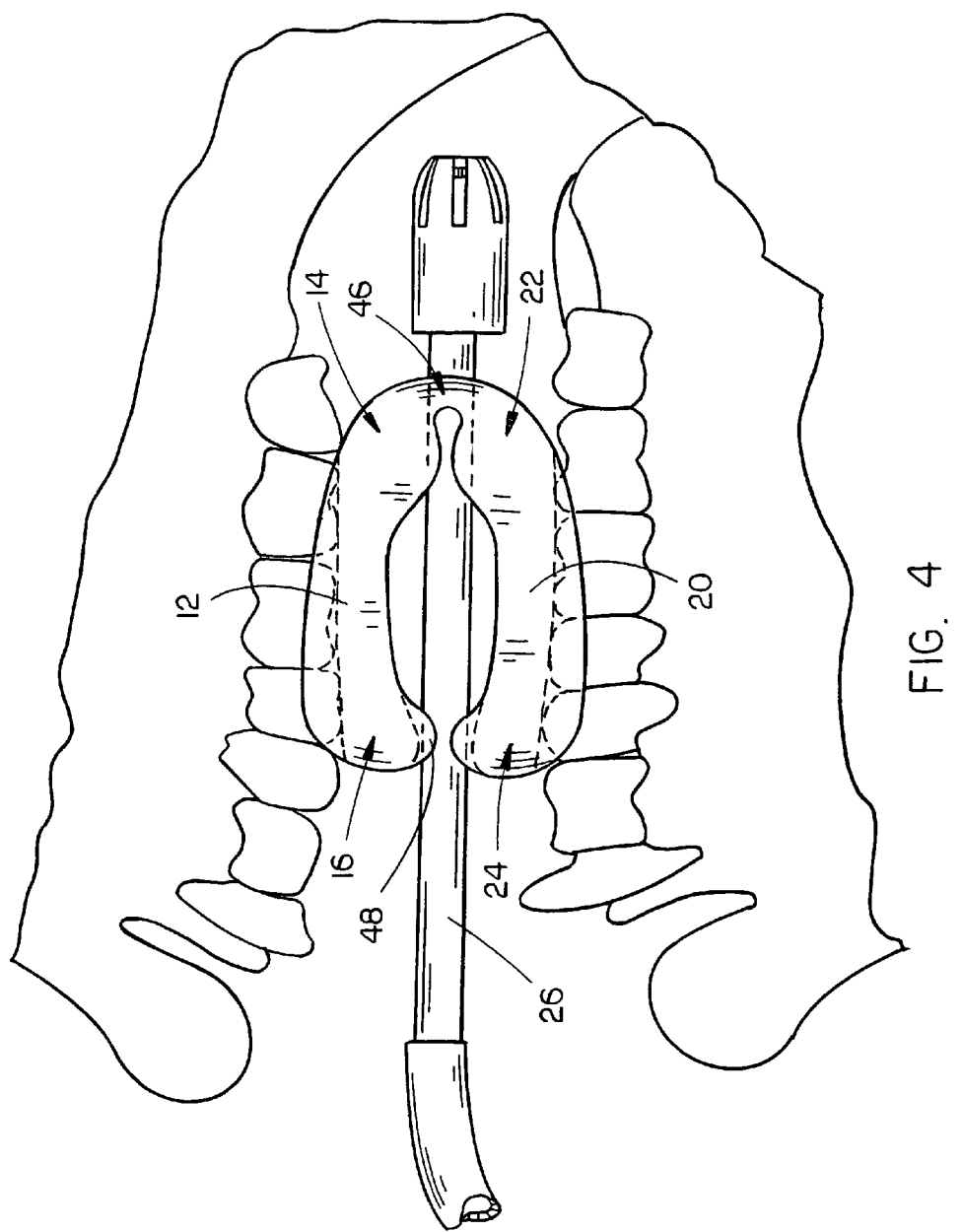
FIG. 4 depicts a side elevation view of one preferred embodiment of the oral suction device as it could be positioned on the left side within an individual's mouth.

The oral suction device 10 of the present invention is generally provided for the removal of fluids and debris from a patient's mouth. A mouth prop 12 is provided as a base component of the device 10 and is preferably shaped and sized to be positioned within the patient's mouth on one side between the upper and lower arcades of teeth, as depicted in FIG. 4. The mouth prop 12, in a preferred embodiment, is provided with a first wing member 14, having a long axis that extends between a first end portion 16 and a second end portion 18. A second wing member 20 is provided in a manner similar to the first wing member 14 in that it too has a long axis extending between a first end portion 22 and a second end portion 24. The first end portion 16 of the first wing member 14 is preferably coupled with the first end portion 22 of the second wing member 20 so that the long axes of the first wing member 14 and the second wing member 20 are angularly disposed with respect to one another, as depicted in FIG. 1.

The device 10 is further provided with an elongated suction tube 26, having a first end portion 28 that is placed in communication with a source of suction, such as those commonly found in most dental offices, and a second end portion 30 that is coupled within an aperture 32 formed within the mouth prop 12. In one preferred embodiment, depicted in FIG. 1, the aperture is positioned closely adjacent the first end portions 16 and 22 of the first and second wing members 14 and 20. The aperture 32 is provided with a peripheral edge portion 34 that is shaped and sized to receive a diameter of the suction tube 26. It may be desirable to removably couple the suction tube 26 within the aperture 32 to permit replacement and cleaning of the component parts. Similarly, it will be desirable to permit the suction tube 26 to be sized in a manner that permits the suction tube 26 to be selectively moved longitudinally in a sliding manner within the aperture 32 so that the second end portion 30 of the suction tube 26 may be selectively positioned with respect to the mouth prop 12. This will permit selective positioning of the mouth prop 12 along the dental arcades while maintaining the ability to position the second end portion 30 of the suction tube 26 in a desirable location within the patient's mouth.

Figure 1:
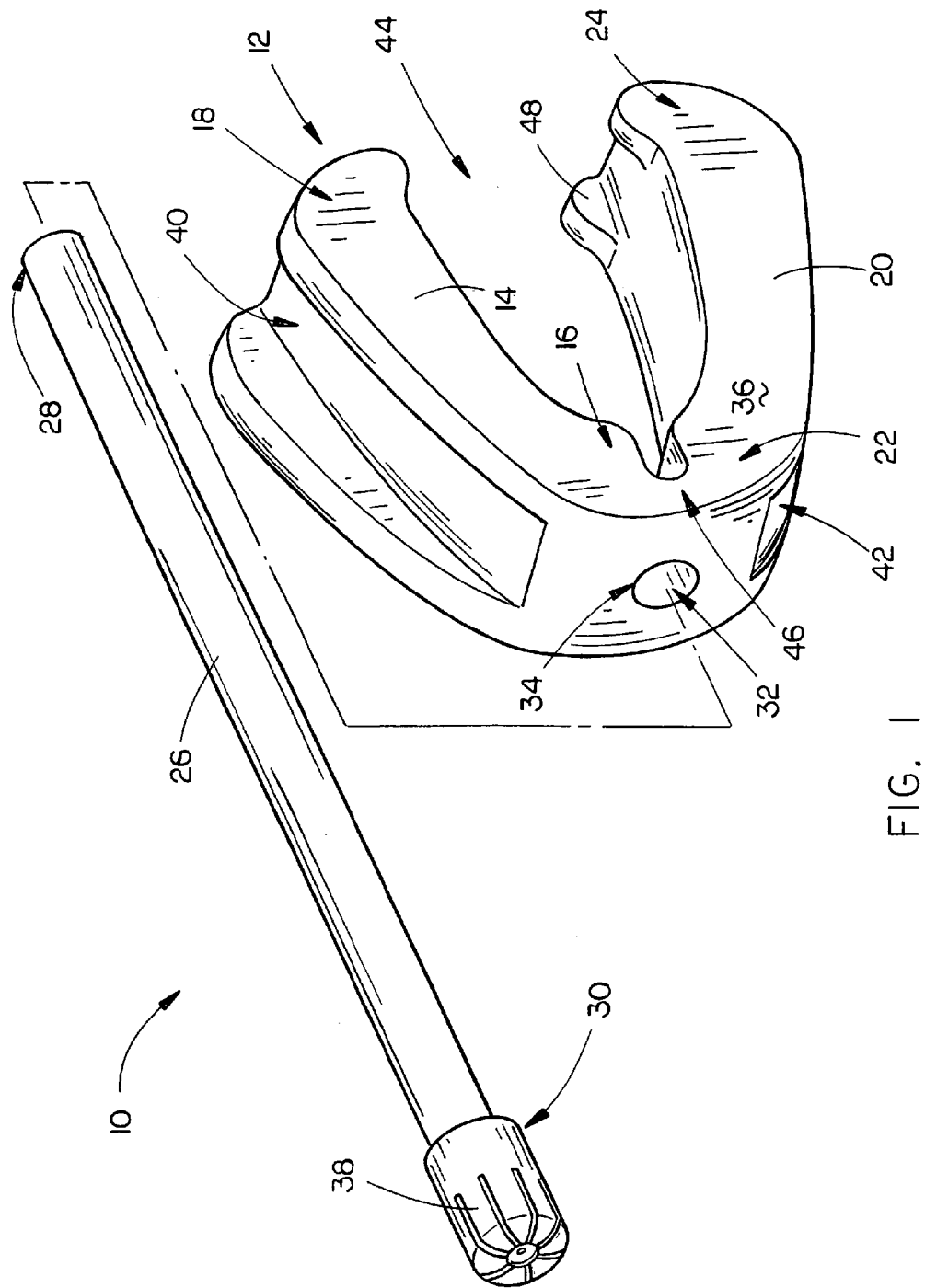
FIG. 1 depicts a perspective view of one preferred embodiment of the oral suction device.

The device 10 depicted in FIG. 1 shows the aperture 32 as being formed coaxially with a long axis of the mouth prop 12 and positioned laterally, such that the peripheral edge portion 34 remains closed. However, in an alternate embodiment, depicted in FIG. 5, the aperture 32 may be formed within the mouth prop 12 such that the peripheral edge portion 34 is open to a side portion 36 of the mouth prop 12. This orientation will permit the suction tube 26 to be passed coaxially through the aperture 32 or transversely through the side portion 36 of the mouth prop 12. Such an embodiment may be more practical where the second end portion 30 of the suction tube 26 is provided with a tip 38 that is larger in diameter than the suction tube 26. In one embodiment, a channel 35 may be formed to place the aperture 32 in open communication with the side portion 36. In such an instance, it may be desirable to provide the channel 35 with a width that is at least slightly more narrow than an outer diameter of the suction tube 26 so that the channel 35 resists the unintentional removal of the tube 26 from the aperture 32 through the side portion 36 of the mouth prop 12. While it is contemplated that the suction tube 26 could be removably secured to the side portion 36 of the mouth prop 12 using some form of bracketry, such a structural arrangement will not be desirable due to potential interference with the patient's tongue or cheek wall. Such positioning of the suction tube 26 will clearly position it to one side of the upper and lower dental arcade, whereas the presently disclosed positioning retains the suction tube 26 substantially in line with the dental arcades.

In a preferred embodiment, the first wing member 14 and the second wing member 20 will be provided with outward faces 40 and 42, respectively, that are positioned to face away from one another. The outward faces 40 and 42 should be pre-shaped to have channels that are generally shaped and sized to releasably receive at least a portion of a patient's upper or lower arcades of teeth on one side. While it is contemplated that the outward faces 40 and 42 could be specifically shaped to receive specific teeth, and position the mouth prop 12 in a specific location within the patient's mouth. A smooth open channel, such as that exhibited by the outward faces 40 and 42 in FIG. 1 will provide a greater versatility in positioning the mouth prop 12 as well as receiving a wide range of differently sized and shaped dental arcades from different patients.

It is contemplated that nearly any type of suction tube 26 may be utilized with the present invention. However, it is contemplated that it may be desirable to form the suction tube 26 from a generally flexible material so that the tube may be shaped during use, to accommodate the different needs presented by a wide array of different patient mouths, without substantially restricting an open passageway extending through the suction tube 26. If may also be desirable to construct the suction tube 26 in a manner that permits the suction tube 26 to be manipulated into a desired shape and retain that same shape. In such an instance, it is contemplated that one or more thin wires may be formed within a length of the suction tube 26 to provide such flexibility and memory. Various known polymers may also be used to form the suction tube 26 to have the same desired characteristics.

Figure 2:
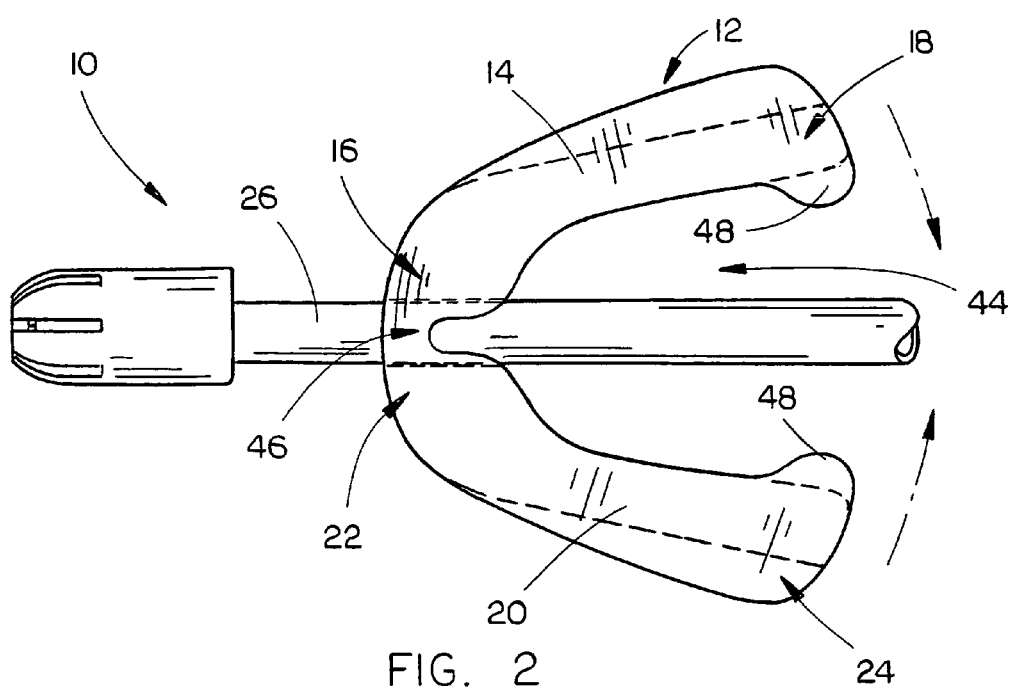
FIG. 2 depicts a side elevation view of the oral suction device depicted in FIG. 1 as it could be positioned in an open position.
Figure 3:
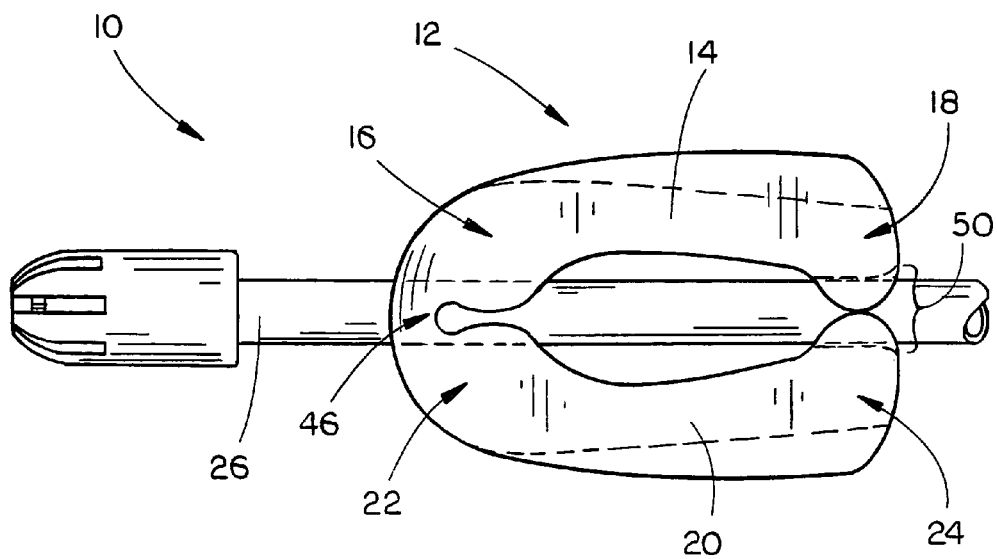
FIG. 3 depicts a side elevation view of the oral suction device depicted in FIG. 1 as it could be positioned in a compressed position.

In one preferred embodiment, the second end portions 18 and 24 of the first wing member 14 and the second wing member 20 are disposed in a spaced-apart relationship with one another and an open cavity 44 is formed between the first wing member 14 and the second wing member 20. It is contemplated that the mouth prop 12 could be formed from nearly any material desired, including various polymers, metals, and the like. However, selection of a deformably resilient material will allow the second end portions 18 and 24 of the first wing member 14 and the second wing member 20 to be manually compressed toward one another, such as depicted in FIGS. 2 and 3. This will permit the patient to bite down onto the mouth prop 12, providing the patient with a certain degree of comfort and control over the degree to which the patient's mouth is propped open. This may further provide the patient with the mental benefit of not feeling as though their jaw is being forced into a confined position. However, it is preferable to shape and size the mouth prop 12 so that when it is in a fully compressed position, such as that depicted in FIG. 4, that the upper and lower dental arcades remain sufficiently spaced apart to permit the dentist to continue working.

Various materials choices for construction of the mouth prop 12 may be limited due to the need to sterilize the device 10, extend the life of the device 10, or provide a desirable degree of rigidity. In such an instance, the available materials may not provide a sufficient resiliency to permit the first wing member 14 and the second wing member 20 to be easily compressed toward one another by the patient's jaw. Accordingly, a hinge 46 may be provided closely adjacent the first end portions 16 and 22 of the first wing member 14 and the second wing member 20 so that they may be more easily compressed toward one another. Many different types of hinges are contemplated for use with the device 10. However, a living hinge, such as that depicted in FIG. 1 may provide a desirable level of durability, longevity, and ease of sterilization. As depicted in FIGS. 2 and 3, the hinge 46 may be easily shaped and sized in a manner that permits movement of the first wing member 14 and the second wing member 20 with respect to one another while maintaining resilient memory to return the mouth prop 12 to an open position.

Figure 5:
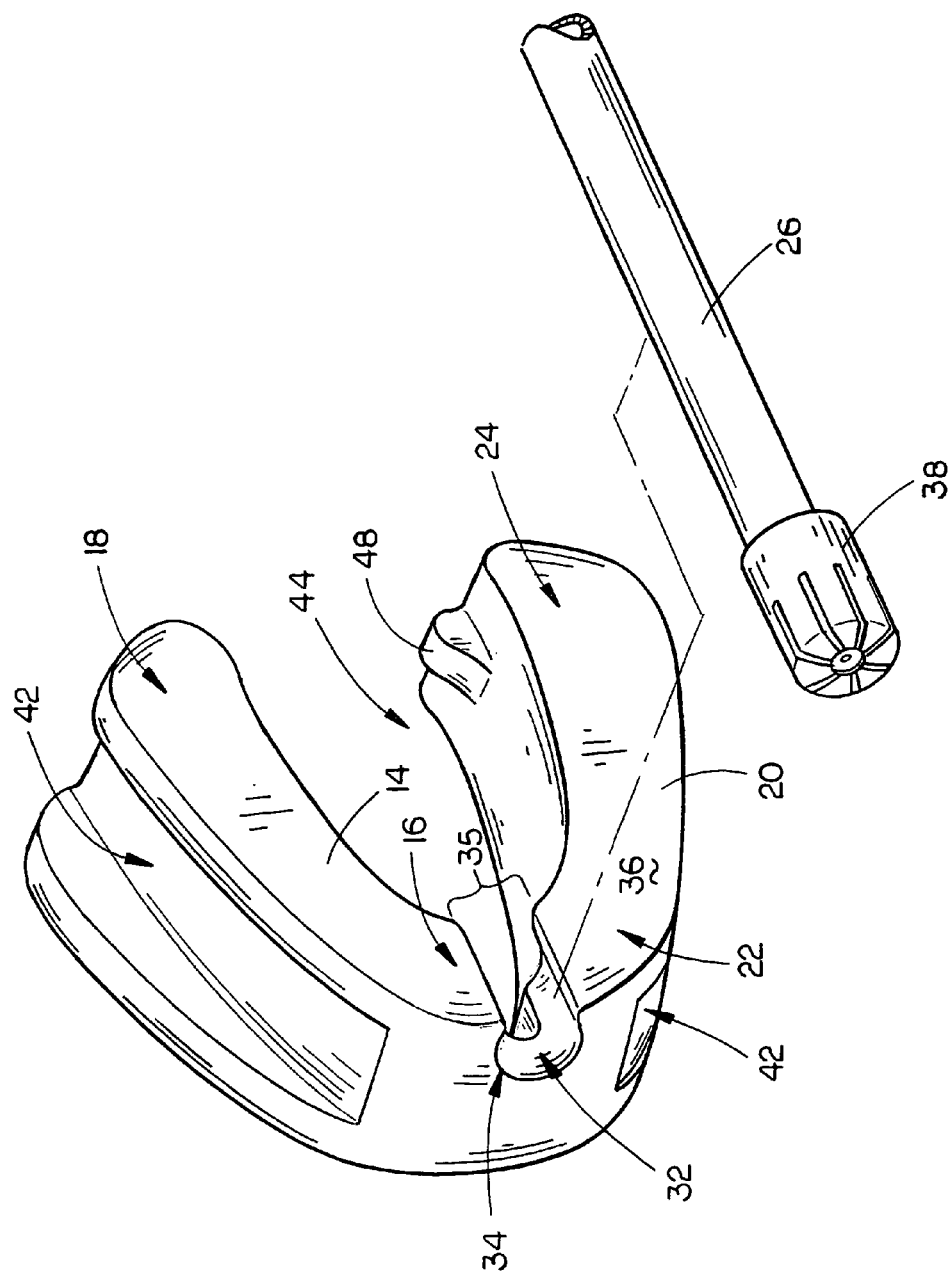
FIG. 5 depicts a perspective view of another preferred embodiment of the oral suction device.

In those embodiments where the first wing member 14 and the second wing member 20 are capable of being manually compressed toward one another, it will be desirable to protect the suction tube 26 from becoming compressed in a manner that restricts the flow through the suction tube 26. Accordingly, in one preferred embodiment, one or more bump-stops 48 may be selectively located within the open cavity 44 so that, as the second end portions 18 and 24 of the first wing member 14 and the second wing member 20 are compressed toward one another, a gap 50 is provided between the first wing member 14 and the second wing member 20 that is sized according to the dimensions of the suction tube 26 so that the suction tube 26 will be substantially uncompressed when the first wing member 14 and the second wing member 20 are moved into a fully compressed position. The size and positioning of the bump-stop 48 may depend upon the position of the suction tube 26 with respect to the mouth prop 12. For example, FIG. 1 depicts pairs of spaced apart bump-stops 48 that permit the suction tube 26 to extend coaxially along a length of the mouth prop 12 and rest between the bump-stops 48 when the mouth prop 12 is in a fully compressed position, such as depicted in FIG. 3. However, a single bump-stop 48 may be positioned intermediate the sides of the mouth prop 12 where the suction tube 26 is positioned closer to one side of the mouth prop 12, such as depicted in FIG. 5. It is contemplated that bump-stops 48 may be positioned on opposing wing members to engage one another when the mouth prop 12 is moved into a fully compressed position. However, it is contemplated that the bump-stops 48 may be positioned to engage nearly any structure along the mouth prop 12 and retain their intended usability.

Although the invention has been described in language that is specific to methodological steps, it is to be understood that the invention defined in the appended claims is not necessarily limited to the specific steps described. Rather, the specific aspects and steps are described as forms of implementing the claimed invention. Since many embodiments of the invention can be practiced without departing from the spirit and scope of the invention, the invention resides in the claims hereinafter appended.

What is claimed is:

1. An oral suction device for the removal of fluid and debris from an individual's mouth, said mouth having a right side and a left side, the device comprising:

a mouth prop adapted to be positioned within the individual's mouth between upper and lower arcades of teeth, each of which arcades has a right side portion and a left side portion, said prop being configured for individual positioning in association with each of said side portions, but with only a single selected one of said side portions at any particular time and having a first wing member, with opposite first and second end portions and a long axis, and a second wing member, with opposite first and second end portions and a long axis; said first end portion of said first wing member being operatively coupled with said first end portion of said second wing member so that the axes of said first and second wing members are angularly disposed with respect to one another; said first and second wing members being provided with outward faces that are positioned to face away from one another; said outward faces being pre-shaped to have channels that are generally shaped and sized to releasably receive any selected one of the side portions; and an elongated tube, having first and second end portions; said first end portion of said tube being placed in communication with a source of suction; said second end portion of said tube being operatively coupled within an aperture formed at least partially within said mouth prop;

said aperture penetrating entirely through said mouth prop and being formed closely adjacent said first end portions of said first and second wing members so that a length of said tube, adjacent the second end portion of said tube, is positioned within said aperture to be generally parallel or coaxial with a long axis of said mouth prop and extend between lengths of the outward faces of said first and second wing members, whereby the length of said tube is substantially in line with the selected side portion of said arcades of teeth such that interference between the length of said tube and a tongue or cheek wall associated with the individual's mouth is substantially prevented; the long axis of said mouth prop extending between the first end portions of said first and second wing members and the second end portions of said first and second wing members.

2. The device of claim 1 wherein said tube is removably coupled with said mouth prop.

3. The device of claim 1 wherein said tube is slidably engaged within said aperture so that the second end portion of said tube may be selectively positioned with respect to said mouth prop.

4. The device of claim 1 wherein said aperture is formed in said mouth prop closely adjacent the first end portions of said first and second wing members.

5. The device of claim 4 wherein said aperture is formed with a closed perimeter so that said tube must be passed coaxially through said aperture.

6. The device of claim 4 wherein said aperture is formed within said mouth prop such that it is provided with a peripheral edge portion that is open to a side portion of said mouth prop so that said tube may be passed coaxially through said aperture or inserted transversely through said side portion of said mouth prop.

7. The device of claim 6 wherein the open portion of the peripheral edge portion of said aperture is in open communication with a channel that is in open communication with said side portion of said mouth prop.

8. The device of claim 7 wherein said channel has a width that is at least slightly more narrow than an outer diameter of said tube so that the channel resists the unintentional removal of said tube from said aperture through said side portion of said mouth prop.

9. The device of claim 1 wherein the second end portions of said first and second wing members are disposed in a spaced-apart relationship with one another and an open cavity is formed between said first and second wing members.

10. The device of claim 9 wherein said first and second wing members are comprised of a deformably resilient material that allows the second end portions of said first and second wing members to be manually compressed toward one another.

11. The device of claim 10 wherein said mouth prop is provided with at least one bump-stop, located within said cavity so that, as the second end portions of said first and second wing members are compressed toward one another, a gap is provided between the second end portions of said first and second wing members that is sized according to dimensions of said tube so that said tube will be substantially uncompressed when the second end portions of said first and second wing members are fully compressed toward one another.

12. The device of claim 9 wherein said mouth prop is provided with a hinge, closely adjacent the first end portions of said first and second wing members so that the second end portions of said first and second wing members may be manually compressed toward one another.

13. The device of claim 12 wherein said hinge is a living hinge, integrally formed as a recess within said mouth prop; said hinge being shaped and sized to permit movement of said first and second wing members with respect to one another but to retain resilient memory.

14. The device of claim 13 wherein said mouth prop is provided with at least one bump-stop, located within said cavity so that, as the second end portions of said first and second wing members are compressed toward one another, a gap is provided between the second end portions of said first and second wing members that is sized according to dimensions of said tube so that said tube will be substantially uncompressed when the second end portions of said first and second wing members are fully compressed toward one another.

15. The device of claim 1 wherein said tube is comprised of a flexible material so that the tube may be shaped during use, without substantially restricting an open passageway within said tube.

16. The device of claim 15 wherein said tube is constructed to permit said tube to be manipulated into a desired shape and retain said shape.

\* \* \* \* \*